United States Patent [19]
Kielmann

[11] Patent Number: 6,130,099
[45] Date of Patent: Oct. 10, 2000

[54] METHOD OF COMPARING PEAK REPRESENTATIONS, SPECIFICALLY WESTERN BLOT OR DOT BLOT STRIPS

[76] Inventor: Ina Matallana Kielmann, Kaiseretrasse 22, 72704 Reutlingen, Germany

[21] Appl. No.: 08/966,092
[22] Filed: Nov. 7, 1997

[30] Foreign Application Priority Data

Nov. 12, 1996 [DE] Germany ............... 196 46 720

[51] Int. Cl.⁷ ............... G01N 33/566; G06K 7/00; G01B 11/28; G01B 11/06
[52] U.S. Cl. ............... 436/501; 436/164; 436/167; 436/171; 436/515; 436/805; 436/541; 235/436; 235/463; 235/454; 235/474; 356/380; 356/381; 356/382
[58] Field of Search ............... 436/501, 515, 436/541, 164, 167, 171, 805; 235/436, 463, 454, 474; 356/380, 381, 382

[56] References Cited

U.S. PATENT DOCUMENTS

| 3,506,818 | 4/1970 | Smith ............... 235/183 |
| 5,210,397 | 5/1993 | Eastman ............... 235/436 |
| 5,293,218 | 3/1994 | Morris et al. ............... 356/382 |

FOREIGN PATENT DOCUMENTS

| 0 172 969 A2 | 3/1986 | European Pat. Off. . |
| 0 395 480 A2 | 10/1990 | European Pat. Off. . |
| 0 670 143 A1 | 9/1995 | European Pat. Off. . |

OTHER PUBLICATIONS

Aldridge P K. et al.: "A Field portable scanner for analysis of thin layer chromatography plates based on multiwavelength image processing", review of scientific instruments, vol. 63, No. 10 PT. 01 Oct. 1, 1992, pp. 4333–4341, XP000316291 * pp. 4335–4336* .

Prosek M et al.: "Quanititative two–dimensional thin–layer chromatography", journal of chromatography, vol. 553, No. 1/02, Aug. 16, 1991, pp. 477–487, XP000316291 * p. 48, col. 1 –col. 2, last paragraph *

Primary Examiner—Christopher L. Chin
Assistant Examiner—Pensee T. Do
Attorney, Agent, or Firm—Henry M. Feiereisen

[57] ABSTRACT

The slope lines of the peak lines are determined for a reference specimen and a test specimen and then compared with one another to analyze peak lines independently of the background. Preferably a minimum amplitude of a slope line is established with a threshold specimen so that fluctuations with a smaller amplitude can be disregarded. This method is suitable especially for automatic analysis of blot strips.

12 Claims, 2 Drawing Sheets

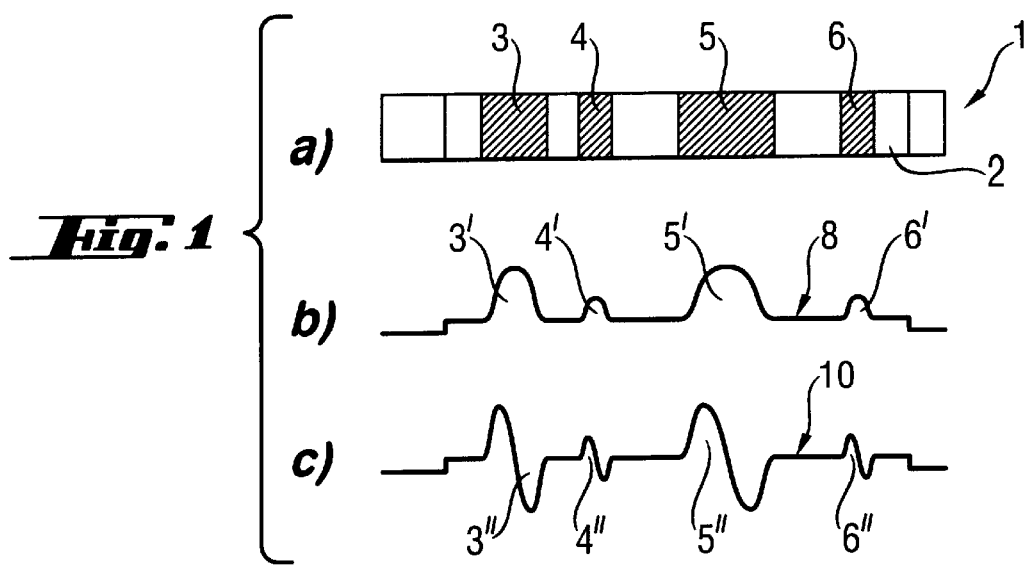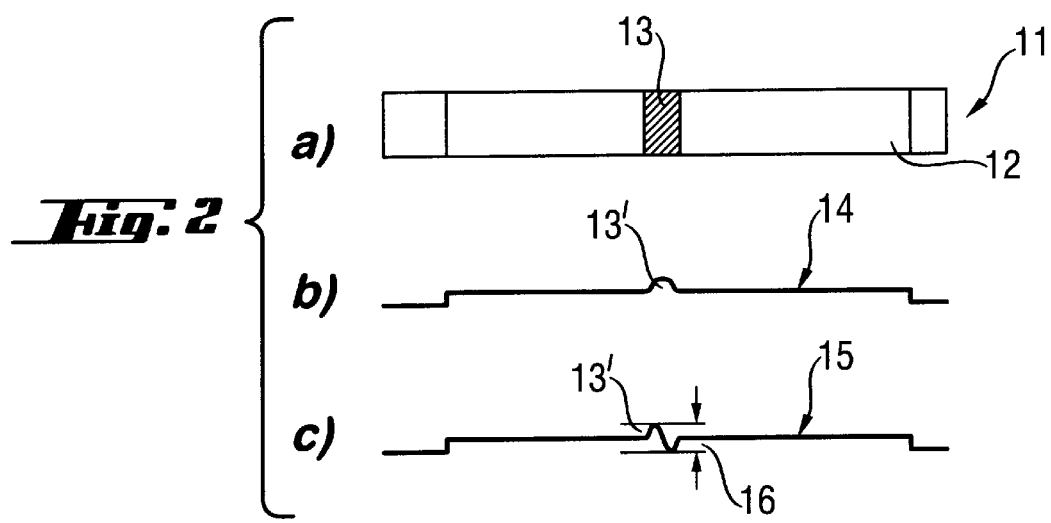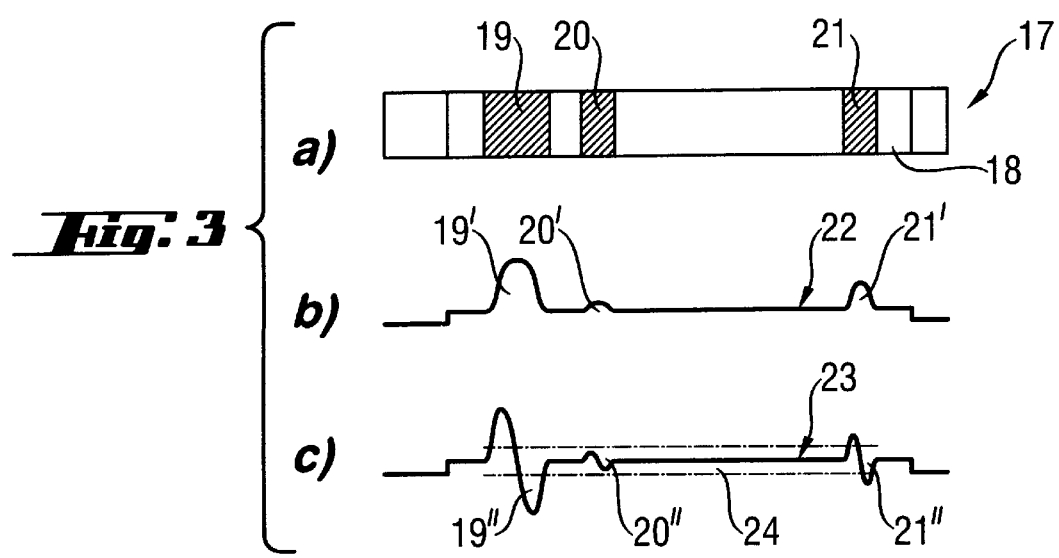

METHOD OF COMPARING PEAK REPRESENTATIONS, SPECIFICALLY WESTERN BLOT OR DOT BLOT STRIPS

BACKGROUND OF THE INVENTION

The invention relates to a method of comparing peak representations, specifically western blot or dot blot strips.

In many technical applications, especially analytical methods, peak diagrams must be compared to deduce a certain result from the comparison of diagrams. This is an especially complicated method, because in peak diagrams, the position, height and area of the two peak diagrams to be compared must be determined to be able to obtain information about their similarity.

Such peak diagrams are used in gas chromatography, for example. However, a common area of application of the comparison of peak diagrams is in comparing chromatographic or electrophoretically stained charts whose chart pattern is detected by an optical sensor. These strip charts are known as western blots or dot blots when antibody reactions on the strips are indicated by different bands.

A special problem in comparing peak diagrams is that the baseline on which the peak diagrams are based is often subject to fluctuations, for example, when a western blot strip whose strip pattern has been scanned has a certain basic coloring. Such differences in basic color of the strip occur, for example, with strips from different manufacturers. However, this can also be attributed to different treatment batches or to differences in storage of the strips.

SUMMARY OF THE INVENTION

Therefore, the object of this invention is to propose a method of comparing peak diagrams with which the inaccuracies described here are eliminated.

This object is achieved with the method according to the present invention, where a slope line of the peak line is determined for a first specimen, the slope line of the peak line is determined for a second specimen, and the slope lines of the specimens are compared with one another.

The invention is based on the finding that a comparison of peak areas can lead to considerable inaccuracies, and this problem is solved by the fact that the derivation of the peak lines is formed, and the fluctuations found in the slope lines are compared with one another. These fluctuations are independent of the background, and therefore they provide a reliable value, even if they both have different background colors than comparable peak diagrams.

An especially advantageous area of application of the method according to the present invention is for the first specimen to be a reference specimen and the second specimen a test specimen. The lack of dependence on the background makes it possible to determine a reference specimen once and compare this reference specimen with different test specimens. Even if the test specimens originate from test strips having different basic colors over the course of lengthy periods of testing, it is not necessary to prepare a reference specimen separately for each basic color, and instead, once a reference specimen has been determined, it can be compared with all test specimens without errors in findings due to different background colors.

The peak lines to be investigated are preferably determined by scanning a test strip. The test strips are detected and digitized by an optical sensor, for example. A flatbed scanner is an example of such a detector.

To determine the slope line from the peak line, it is proposed that the slope be determined as the change in contrast using an image processing device. Such programs for determining contrast are known and can be used with the method according to this invention.

To eliminate conventional, irrelevant changes in contrast attributed to blotches or systematic errors, fluctuations in slope line whose amplitude is below a certain level may be disregarded in comparing the slope lines. The minimum value of an amplitude of the slope line to be taken into account may be set once or it may be variable.

To establish this minimum amplitude value, it is proposed that the slope line of the peak line and the amplitude of the slope line be determined for a threshold specimen, and that all fluctuations on the second specimen with a smaller amplitude of the slope line be disregarded. This makes it possible to set the limit amplitude value by means of a threshold specimen in a simple way.

One possibility of analysis of the comparison according to the present invention is to prepare a data record from the position and type of fluctuations in the slope lines. These values can be determined through filter systems, where the position, amplitude and preferably also the frequency of the fluctuations tested are documented in the data record.

An alternative method of obtaining a data record is to compare the fluctuations of the slope lines with one another by a comparison of patterns and then derive a data record for the correspondence. A pattern comparison, which can be done by filter systems, neural systems or fuzzy systems, for example, makes it possible to obtain a data record with very accurate values for correspondence between the specimens compared.

The invention provides for proposed findings to be attributed to the data record obtained in this way. The proposed findings lead to an evaluation of the data record obtained by the method according to the present invention which can be used directly in practice.

To make the method especially user-friendly, it is ultimately proposed that the data record be transferred with a parser to text findings, preferably with graphics. This leads to the result that the user of the method according to the present invention receives an automatically prepared text wherein the comparison of peak diagrams is described, and preferably the result obtained is also evaluated.

DETAILED DESCRIPTION OF PREFERRED EMBODIMENTS

An exemplified embodiment of the method according to the present invention is described in greater detail below with reference to the drawing, in which:

FIG. 1 shows a test strip, a peak diagram and a slope line of a reference specimen;

FIG. 2 shows a test strip, a peak diagram and a slope line of a threshold specimen;

FIG. 3 shows a test strip, a peak diagram and a slope line of a test specimen.

Figure 4:
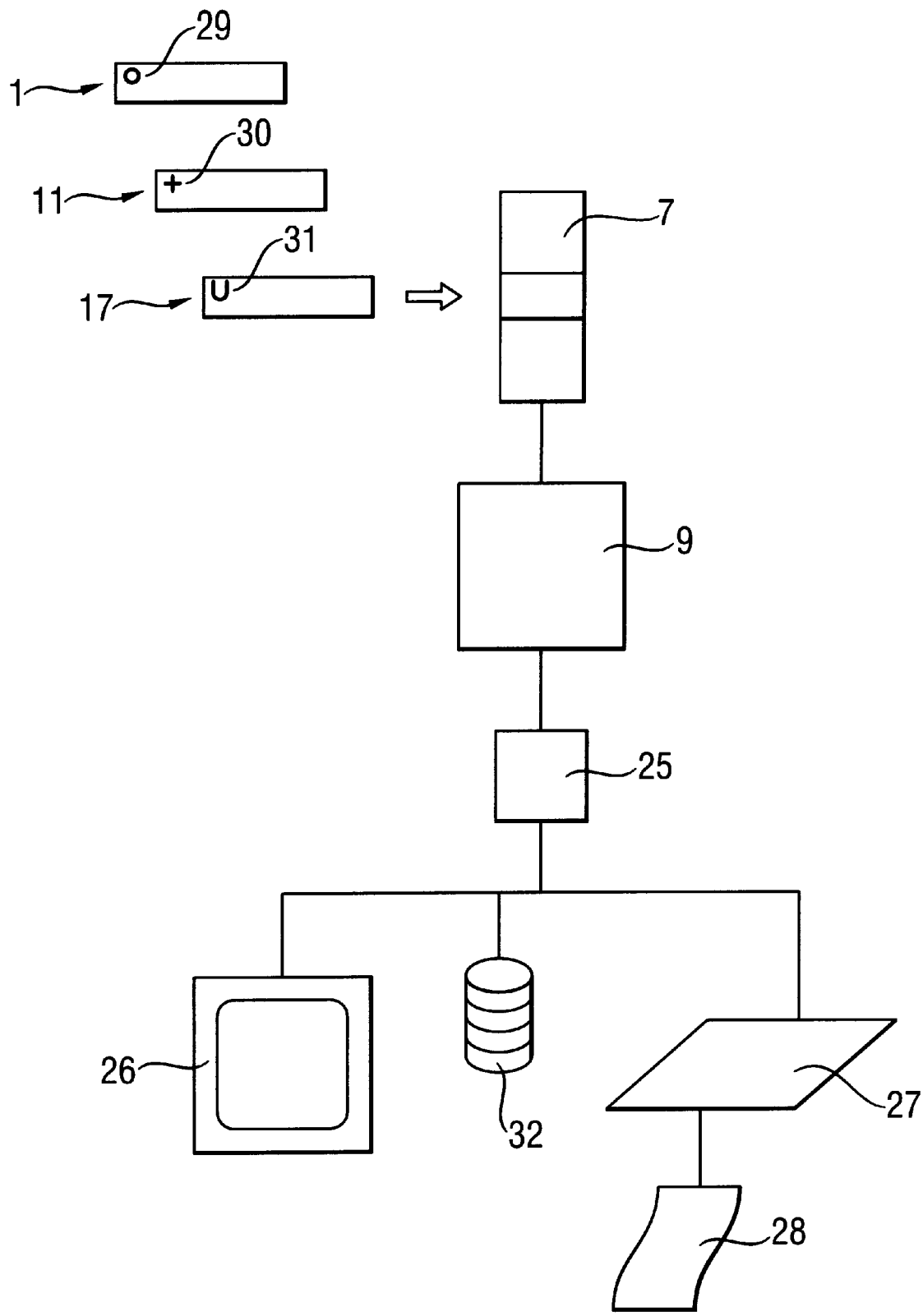
FIG. 4 shows a schematic diagram of the method.

The first specimen 1 shown in FIG. 1a is a reference specimen wherein bands 3, 4, 5, 6, which are a different color from the background, have been produced on a reference strip 2 by antibody reactions.

When this reference specimen 1 is analyzed with a scanner 7 (see FIG. 4), the latter yields a peak line 8, which is shown in figure 1b. A peak 3', 4', 5', 6' is assigned to each band 3, 4, 5, 6.

Slope line 10, which is shown in FIG. 1c, is calculated from peak line 8 by a computer 9 (see FIG. 4). A fluctuation 3", 4", 5", 6" on slope line 10 corresponds to each band 3, 4, 5, 6 on reference specimen 1.

A threshold specimen 11, which is shown in FIG. 2a, serves to establish a threshold value. Somewhere on threshold strip 12, this specimen has a band 13 whose change in contrast against the background is set so that it indicates the minimum change in contrast which is needed to be able to deduce an immune reaction with certainty. This threshold specimen 11 can also be passed through scanner 7 to obtain a peak line 14, which is shown in FIG. 2b. A peak 13' on this peak line 14 corresponds to band 13. This peak line 14 is also converted to a slope line 15 by computer 9 (see FIG. 4). This slope line 15 is shown in FIG. 2c, where fluctuation 13" with an amplitude 16 corresponds to band 13.

The slope line 10 of reference specimen 1 thus determined and the amplitude 16 of threshold specimen 11 are stored in computer 9 and used later to evaluate a second specimen 17, namely the test specimen.

A test strip 18 having bands 19, 20, 21 formed by immune body reactions is illustrated as test specimen 17 in FIG. 3a. Test strip 19 is also run through scanner 7 as test specimen 17 to determine peak line 22 which is shown in FIG. 3b. Peak line 22 has three peaks 19', 20' and 21' which correspond to bands 19, 20 and 21 on the test strip.

A slope line 23, as illustrated in FIG. 3c, is calculated from peak line 22 by computer 9. A fluctuation 19" on slope line 23 corresponds to band 19, fluctuation 20" corresponds to band 20 and fluctuation 21" corresponds to band 21. Corresponding to amplitude 16 shown in FIG. 2c, FIG. 3c shows a fluctuation range 24 bordered by dash-dot lines. Fluctuations such as fluctuation 20" which are within fluctuation range 24 are below the threshold determined by threshold specimen 11 and are not taken into account in a comparison of slope line 23 of test specimen 17 with slope line 10 of reference specimen 1.

After obtaining slope line 23 of test specimen 17, slope line 23 is compared with slope line 10 of reference specimen 1 by a pattern comparison performed in computer 9. Fluctuations 20" which are within fluctuation range 24 are not taken into account, and fluctuations 19", 21" which correspond to a fluctuation 3", 6" on slope line 10 of reference specimen 1 are transferred as a data record to a parser 25 which transmits the data record to a text of findings. This text of findings can either be displayed on a screen 26, output as protocol 28 by a printer 27 or stored on a storage medium 32, such as a hard disk.

To better assign and transmit additional information, strips 1, 11, and 17 bear marks such as characters and notation 29, 30, 31 which are entered with scanner 7 and are included in the data record. These marks may be used to prepare the text of findings or they may serve to identify different types of strips.

What is claimed is:

1. A method of comparing peak features of electrophoretic Blot diagrams comprising:

determining a slope line of a peak feature for a first specimen determining a slope line of a peak feature for a second specimen and comparing the slope line of the first specimen with the slope line of the second specimen.

wherein the peak features of the first and second specimen represent a spatial optical contrast of the respective electrophoretic Blot diagram.

2. The method according to claim 1, wherein the first specimen is a reference specimen, and the second specimen is a test specimen.

3. The method according to claim 1, wherein the peak features are determined by scanning the Blot diagram.

4. The method according to claim 3, wherein marks are determined by scanning the strips.

5. The method according to claim 1, wherein the slope lines are determined from a change in contrast using an image processing device.

6. The method according to claim 2, wherein a reference amplitude of the slope line is determined for the reference specimen, and a test amplitude of the slope line of the test specimen which is smaller than the reference amplitude is disregarded.

7. The method according to claim 6, wherein a data record is obtained from the test amplitude and a position of the slope line of the test specimen.

8. The method according to claim 7, further comprising preparing a data record based on the test amplitude and the position of the slope line of the test specimen.

9. The method according to claim 7, wherein the data record is analyzed and transmitted through a parser to at least one of a display screen, a printer and a storage medium.

10. The method according to claim 7, a parser is used to transmit the data record to a text of findings.

11. The method according to claim 8, wherein proposed findings are attributed to the data record.

12. The method according to claim 8, wherein a parser is used to transmit the data record to a text of findings.

* * * * *